(12) United States Patent
Carroll

(10) Patent No.: US 7,867,281 B2
(45) Date of Patent: *Jan. 11, 2011

(54) METALLIC BEARINGS FOR JOINT REPLACEMENT

(75) Inventor: Michael E. Carroll, Memphis, TN (US)

(73) Assignee: Wright Medical Technology Inc, Arlington, TN (US)

(*) Notice: Subject to any disclaimer, the term of this patent is extended or adjusted under 35 U.S.C. 154(b) by 352 days.

This patent is subject to a terminal disclaimer.

(21) Appl. No.: 12/106,674

(22) Filed: Apr. 21, 2008

(65) Prior Publication Data

US 2008/0200988 A1  Aug. 21, 2008

Related U.S. Application Data

(63) Continuation of application No. 10/965,491, filed on Oct. 14, 2004, now Pat. No. 7,361,194.

(51) Int. Cl.
  A61F 2/32 (2006.01)
  A61F 2/30 (2006.01)
(52) U.S. Cl. .................. 623/22.15; 623/23.53
(58) Field of Classification Search .............. 623/22.15, 623/23.53–23.55
  See application file for complete search history.

(56) References Cited

U.S. PATENT DOCUMENTS

| | | | |
|---|---|---|---|
| 6,120,545 A | 9/2000 | Hamelijnck |
| 6,582,436 B2 | 6/2003 | Schlapfer |
| 6,652,588 B2 | 11/2003 | Hayes |
| 6,974,483 B2 * | 12/2005 | Murray | 623/22.42 |

FOREIGN PATENT DOCUMENTS

| | | |
|---|---|---|
| EP | 0310566 A2 | 5/1989 |
| EP | 0841041 A2 | 5/1998 |
| WO | WO01/17464 | 3/2001 |
| WO | WO03/093527 | 11/2003 |

OTHER PUBLICATIONS

Firkins, P.J., et al.: A novel low wearing differential hardness, ceramic-on-metal hip joint prosthesis. J. Biomechanics 34: 1291-1298 (2001).

(Continued)

*Primary Examiner*—William H Matthews
*Assistant Examiner*—Marcia Hoffman

(57) ABSTRACT

An orthopedic prosthesis comprising a first component having a soft metal bearing surface and a second component having a hard metal bearing surface, in particular a hip prosthesis comprising a spherical bearing member, a femoral stem, and a modular neck configured for interposition between the spherical bearing member and the stem, together with an acetabular implant having a concave bearing surface configured for articulation with the spherical bearing member. One of the spherical bearing member and the concave bearing surface comprises a soft metal bearing surface, the soft metal bearing surface having a hardness of at least about 20 Rc, while the other one of the spherical bearing member and the concave bearing surface comprises a hard metal bearing surface, the hard metal bearing surface having a hardness greater than the soft metal bearing surface by at least about 15 Rc.

20 Claims, 6 Drawing Sheets

OTHER PUBLICATIONS

Medley, J.B., et al.: Comparison of alloys and designs in a hip simulator study of metal on metal implants. Clin. Orthop. Rel. Res. 329S: S148-S159 (1996).

Savarino, L., et al.: Ion release in stable hip arthroplasties using metal-on-metal articulating surfaces: A comparison between short- and medium-term results. J. Biomed. Mater. Res. 66A: 450-456 (2003).

Santavirta, S.: Compatibility of the totally replaced hip. Reduction of wear by amorphous diamond coating. Acta Orthop Scand Suppl. 74(310): 1-19 (2003).

Fisher, J., et al. Wear of surface engineered metal-on-metal hip prostheses. J. Mater. Sci. Mater. Med. 15(3): 225-235 (2004).

Author Unknown: Cobalt and Cobalt Alloys. Knowledge Article from www.key-to-metals.com (2004).

Product Brochure: Metal-on-metal articulation and wear. Wright Medical Technology, Inc., Arlington, Tennessee, USA (2004).

Clarke, I.C., et al.: Ultra-low wear rates for rigid-on-rigid bearings in total hip replacements. Proc. Inst. Mech. Eng [H] 214(4): 331-347 (2000).

International Search Report, PCT International Search Report mailed Feb. 21, 2006 for PCT/US2005/036899 (filed Oct. 13, 2005).

* cited by examiner

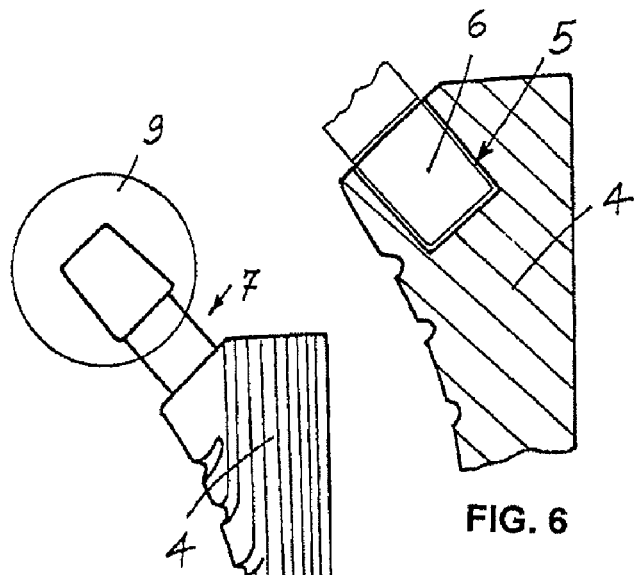
FIG. 6
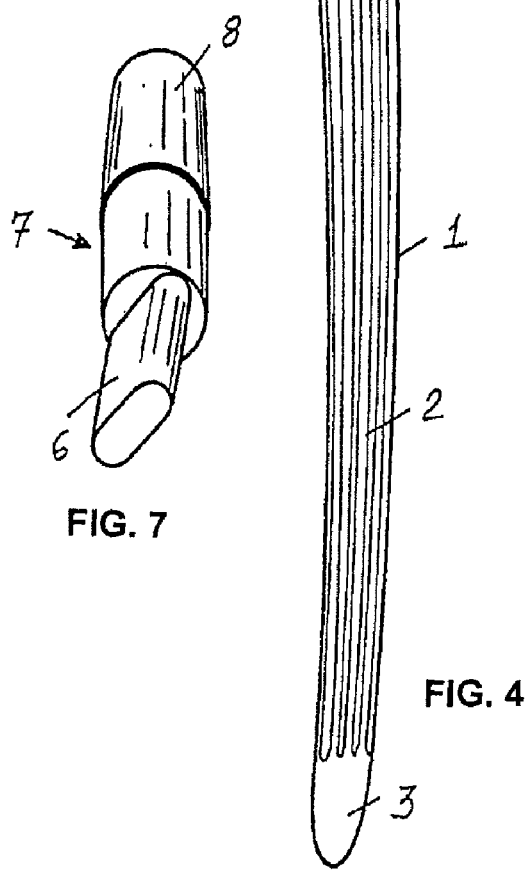
FIG. 4
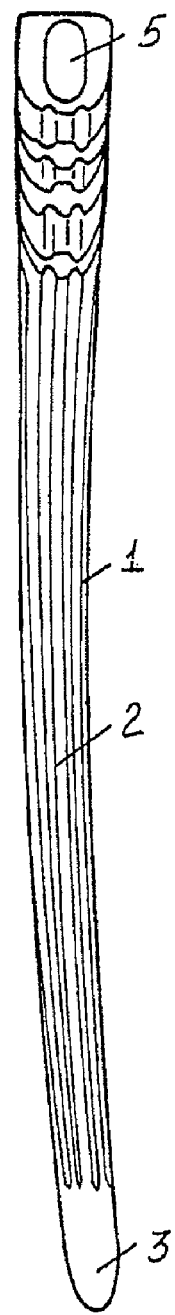
FIG. 5
FIG. 7

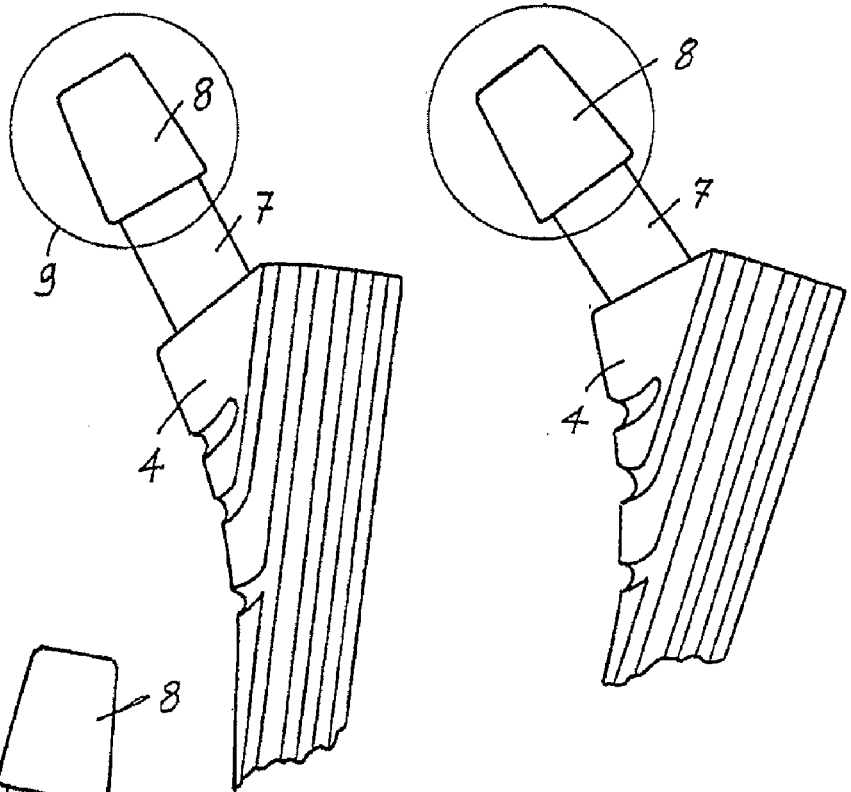
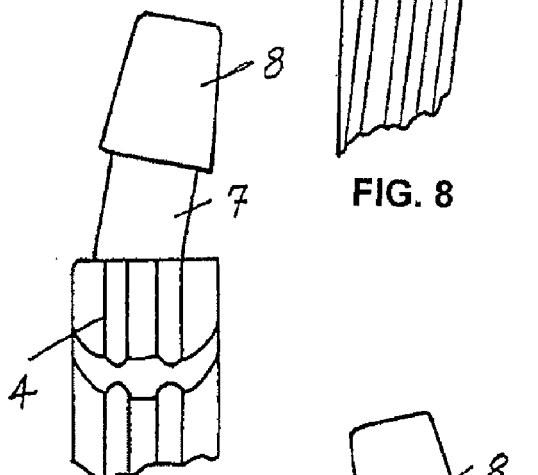
FIG. 8
FIG. 9
FIG. 10
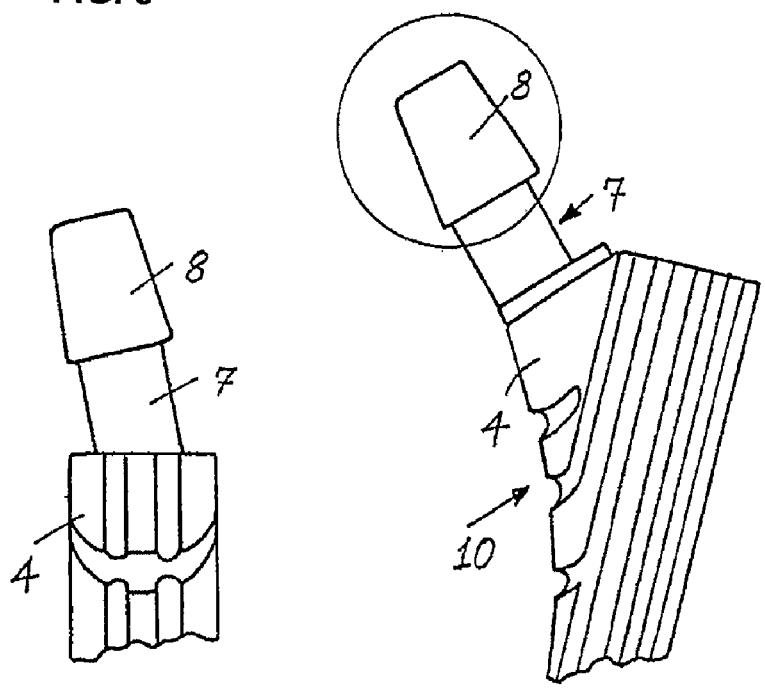
FIG. 11
FIG. 12

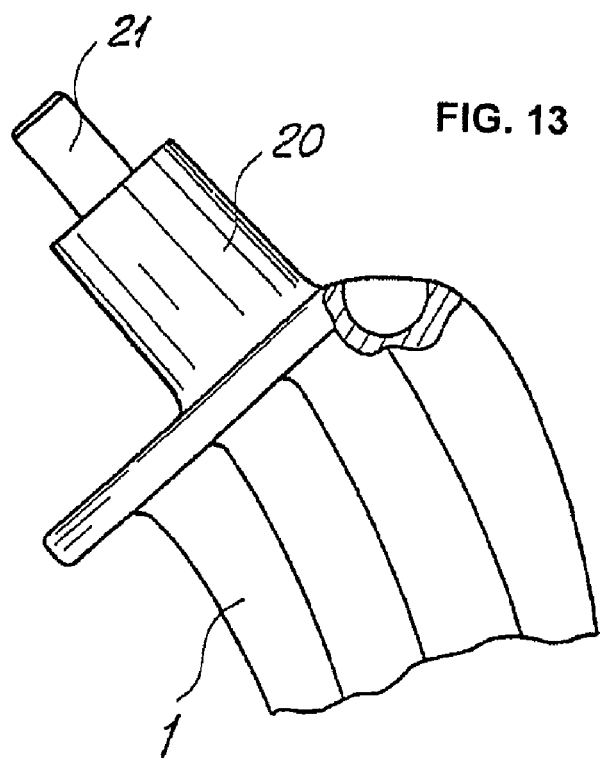
FIG. 13
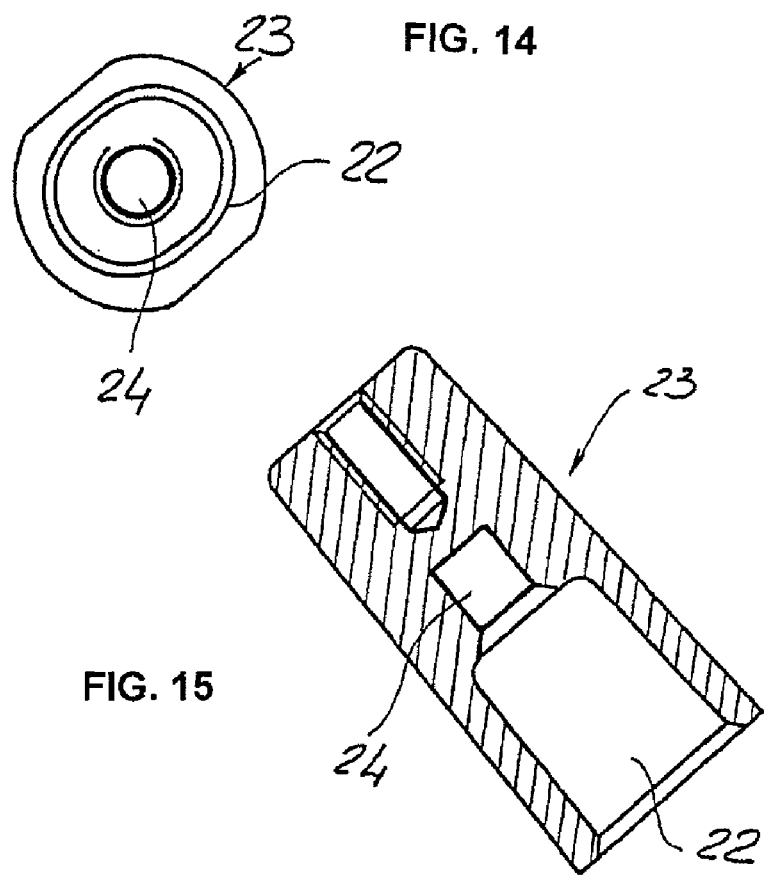
FIG. 14
FIG. 15

METALLIC BEARINGS FOR JOINT REPLACEMENT

CROSS REFERENCE TO RELATED APPLICATIONS

This application is a continuation of and claims priority to U.S. Pat. App. Ser. No. 10/965,491, now U.S. Pat. No. 7,361,194 filed Oct. 14, 2004.

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to orthopedic prostheses, and more particularly to prostheses having differential hardness metal bearings in order to decrease wear debris and increase the useful life of the prostheses.

BACKGROUND OF THE INVENTION

Orthopedic joint prostheses are used to replace diseased joints, such as in the hip, knee, ankle or shoulder. An orthopedic joint prosthesis includes bearing surfaces that allow for articulation similar to that provided by the articulating surfaces of a natural joint.

One problem associated with orthopedic joint prostheses is wear of the bearing components. During articulation, the bearing surfaces slide against each other under load, which results in wear of the bearing surfaces, including loss of minute particles from the bearing surfaces. Over time, such particulates accumulate in the body of the patient, where it is theorized that the particles may cause adverse physiological reactions in some patients. Additionally, gradual loss of particulates results in erosion of the bearing surfaces, which may eventually lead to failure of the prosthesis. Various efforts have been made to minimize wear debris in joint prostheses. In recent years, efforts have focused on the use of metal-on-metal ("MOM") joint prostheses, in which both of the articulating surfaces are metal, and ceramic-on-metal ("COM") prostheses, in which one of the articulating surfaces is ceramic and the opposing surface is metal, and ceramic-on-ceramic ("COC") prostheses, in which both of the articulating surfaces are ceramic.

Lower wear is expected with COC and COM combinations due to the increased abrasion resistance provided by the hard ceramic materials. Differences in material stiffness, especially in COM combinations, have been shown to facilitate bearing lubrication with resulting decreased wear. Additionally, COM bearing combinations have a relatively high hardness differential ranging from about 3× to about 5×, and typically on the order of 4×, which is thought to contribute to lower wear rates.

Despite the low wear properties of COM and COC prostheses, ceramic heads present a risk of fracture, a risk that may steer some surgeons away from COM prostheses, despite the benefits of low wear. In addition, the brittleness and lower toughness of ceramic materials make it difficult to manufacture large diameter femoral heads of the type used in resurfacing procedures. MOM prostheses produce less wear particles than conventional metal-on-polymer ("MOP") prostheses. MOM joint prostheses are typically made of cobalt based alloys conforming to ASTM F75 and/or F1537 specifications. In conventional MOM joint prostheses, the opposing bearing surfaces are made of the same cobalt chrome alloy and therefore have substantially the same hardness (typically, ranging from about 25 to 45 Rc). Thus far, little attention has been paid to the hardness of the MOM bearing surfaces. Factors other than hardness were thought to have a greater effect on wear rate in MOM hip prostheses. The most important wear factors are surface finish, clearance, and sphericity. Recent efforts to improve the performance of MOM joint prostheses have therefore focused on improving surface finish, clearance, and sphericity, rather than on the hardnesses of the cobalt chrome bearing surfaces.

Although MOM prostheses have lower wear volumes than MOP prostheses, metal wear particles are very small and high in number, and the physiological effect of metal wear particles is not fully understood. There is thus an interest in further reducing the volume of wear particles from MOM prostheses.

In ceramic-on-metal ("COM") joint prostheses, the ceramic bearing surface is significantly harder than the metal bearing surface, and therefore necessarily provides a hybrid bearing effect. WO 01/17464A1 (Fisher et al.) discusses improved wear in orthopedic prostheses through the use of COM. WO 01/17464A1 disclosed that materials of the two surfaces can be selected with hardnesses that are greater than those in other joint systems so that the tendency for them to wear during articulation is reduced, and with a differential hardness which can ensure that one of the surfaces is generally able to remain smooth during articulation. This in turn can result in low wear of the opposite surface. WO 01/17464A1 noted that the use of a ceramic material that is significantly harder than the metal material has the advantage that the tendency of the ceramic material to wear during articulation is minimized. WO 01/17464 included wear testing data showing that wear debris from a COM prosthesis was significantly less than from a MOM prosthesis. According to WO 01/17464, the MOM prosthesis showed a bedding-in wear rate of $3.12 \pm 0.45$ mm$^3$/10$^6$ cycles for about the first million cycles, which settled down to a steady state wear rate of $1.56 \pm 0.78$ mm$^3$/10$^6$ cycles. In contrast, the COM prosthesis showed essentially no bedding-in phase and a steady state wear rate of about 0.01 mm$^3$/10$^6$ cycles over the course of a 3 million cycle test. Substantially all of the wear debris from the COM components was metal.

Further data comparing COM and MOM hip prostheses is provided in *A Novel Low Wearing Differential Hardness, Ceramic-On-Metal Hip Joint Prosthesis*, 34 J'1 of Biomechanics, 1291-1298 (2001) (Firkins et al.). The Firkins article reported wear rates for MOM prostheses that showed a 100 fold higher degree of wear than for COM prostheses. Id. at 1296. Firkins tested femoral heads manufactured from medical grade alumina (ISO 6474) and femoral heads manufactured from medical grade low carbon (less than 0.07 percent) wrought cobalt chrome alloy (ASTM F1537). Id. at 1293. Firkins coupled the ceramic and cobalt chrome heads with acetabular cups manufactured from medical grade high carbon (greater than 0.2 percent) wrought cobalt chrome alloy (ASTM F1537). Id. at 1293. Firkins reported a bedding in rate for MOM prostheses of $3.09 \pm 0.46$ mm$^3$/10$^6$ cycles during the first million cycles and a steady state wear rate of $1.23 \pm 0.5$ mm$^3$/10$^6$ cycles. Id. at 1294. The overall wear rate for MOM prostheses during the test was 1.62 mm$^3$/10$^6$ cycles. Id. at 1294. Firkins noted that about 70 percent of the wear on the MOM prostheses occurred on the low carbon cobalt chrome heads. Id. at 1294. In contrast with MOM prosthesis wear, Firkins reported a wear rate on the COM prostheses of 0.1 mm$^3$/10$^6$ cycles during a five million cycle test. Id. at 1294. The results of Firkins thus suggest that MOM prostheses wear at a rate 100 times greater than that of COM prostheses. Id. at 1294-96.

European Patent Application 841 041 A2 (Farrar) reported improved wear if the two articulating surfaces of a metal-on-metal prosthesis are formed from metals which are mismatched with respect to their carbon content. According to EP 841 041A2, testing of MOM hip prostheses having mismatched carbon contents demonstrated that the lowest average wear (weight loss) was observed for prostheses in which a low carbon content alloy was used for the femoral head and a high carbon content alloy was used for the acetabular cup, or vice versa. (Col. 4, lines 46-53). EP 841 041 A2 reported that the highest average wear was observed for prostheses in which the femoral head and acetabular cup were both formed from low carbon content alloy or both formed from high carbon content alloy. (Col. 4, lines 46-53). A1 though EP 841 041 A2 reported testing of MOM prostheses for up to two million cycles, the patent failed to report actual wear test data, and it therefore impossible to quantitatively evaluate the wear claims made in the patent.

EP 841 041 A2 did not note a difference in hardness between the mismatched carbons. This is probably because CoCrMo alloys with low carbon contents of different carbon contents have essentially the same hardness values. For example, a CoCr with a low carbon content of 0.07 percent-by-weight can have a hardness of 41 Rc, while a CoCr with a high carbon content of 0.25 percent-by-weight can have a hardness of 42 Rc.

In the general field of metal bearings, hybrid bearings consisting of a hard metal bearing in combination with a soft metal bearing have long been used to reduce wear of the bearing components. However, the hardness differential of hybrid bearings is provided by forming the bearing surfaces from two different types of metal, rather than from the same type of metal.

Despite prior art COM prostheses that by default have differential hardness bearing surfaces due to the use of different materials for the two bearing surfaces, no attempt has been made to explore the extent to which differential hardness concepts apply to the wear of MOM prostheses. There is thus a need for a joint prosthesis having the following characteristics and advantages over the prior art.

OBJECTS AND SUMMARY OF THE INVENTION

It is an object of the invention to provide an MOM orthopedic joint prosthesis that reduces wear through the use of differential hardness.

It is another object of the invention to provide a MOM orthopedic joint prosthesis that reduces the volume of wear debris in a recipient of the prosthesis through the use of cobalt chrome alloys that are currently used for joint prostheses.

These and other objects of the invention are achieved by providing an orthopedic joint prosthesis comprising a first component having a soft metal bearing surface and a second component having a hard metal bearing surface. The soft metal bearing surface has a hardness of at least about 20 Rc, while the hard metal bearing surface having a hardness greater than the soft metal bearing surface by at least about 15 Rc. The soft and the hard metal bearing surfaces are configured to articulate with one another. The differential hardness of the hard metal bearing surface to the soft metal bearing surface is preferably at least about 1.5, and is preferably less than about 3. The hard metal bearing surface is preferably not more than about 40 Rc harder than the soft metal bearing surface. The hard metal bearing surface preferably has a hardness of between about 40 Rc and about 60 Rc.

In one preferred embodiment, the concepts of the invention are used in a hip prosthesis comprising a spherical bearing member, the spherical bearing member having a neck recess therein; a femoral stem, the femoral stem having a recess adjacent a proximal end thereof, a modular neck member, a proximal end of the modular neck member configured to fixedly engage the neck recess of the spherical bearing member, a distal end of the modular neck member configured to fixedly engage the recess of the stem; and an acetabular implant having a concave bearing surface configured for articulation with the spherical bearing member. One of the spherical bearing member and the concave bearing surface comprises a soft metal bearing surface of cobalt chrome alloy, the soft metal bearing surface having a hardness of at least about 20 Rc, while the other one of the spherical bearing member and the concave bearing surface comprises a hard metal bearing surface of cobalt chrome alloy, the hard metal bearing surface having a hardness greater than the soft metal bearing surface by at least about 15 Rc, such that there is a hardness differential between the spherical member and the concave bearing surface to thereby reduce wear of the hip prosthesis. In one preferred embodiment, the spherical bearing member has a diameter of between about 40 mm to about 60 mm, such as 54 mm.

The foregoing and other objects, features, aspects and advantages of the invention will become more apparent from the following detailed description of the invention when considered in conjunction with the accompanying drawings.

BRIEF DESCRIPTION OF THE DRAWINGS

FIG. 4 shows a side view of a modular neck hip prosthesis structure that can be used with the differential hardness concept of the present invention.

FIG. 5 shows a front view of one embodiment of a modular neck hip prosthesis stem.

FIG. 6 is a cross-sectional view illustrating a coupling between the stem and a coupling member/modular neck of the prosthesis.

FIG. 7 shows a possible embodiment of the prosthesis coupling member/modular neck.

FIG. 8 shows one embodiment of a straight modular neck.

FIG. 9 shows one embodiment of a varus modular neck.

FIG. 10 shows one embodiment of a retroverted modular neck.

FIG. 11 shows one embodiment of an anteverted modular neck.

FIG. 12 shows one embodiment of a lateralized/medialized offset modular neck.

FIG. 13 shows one embodiment of a prosthesis stem configured for receipt of a coupling member;

FIG. 14 is an end view of a coupling member to be used with the prosthesis stem illustrated in FIG. 13.

FIG. 15 is a cross-sectional view of a coupling member to be used with the prosthesis stem illustrated in FIG. 13.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

The invention is an orthopedic joint prosthesis in which the material of one of the bearing surfaces is a metal material and the material of the other bearing surface is a metal material having a different hardness than that of the other bearing surface. For the sake of consistency and clarity in the discussion of this invention, the bearing surface having the softer metal will be referred to as the "soft metal bearing surface," while the bearing surface comprising the harder metal will be referred to as the "hard metal bearing surface." Of course "soft" and "hard" metal bearing surface are relative terms, and they are used herein to describe a hardness relationship between the bearing surfaces, rather than an absolute physical property.

Figure 1:
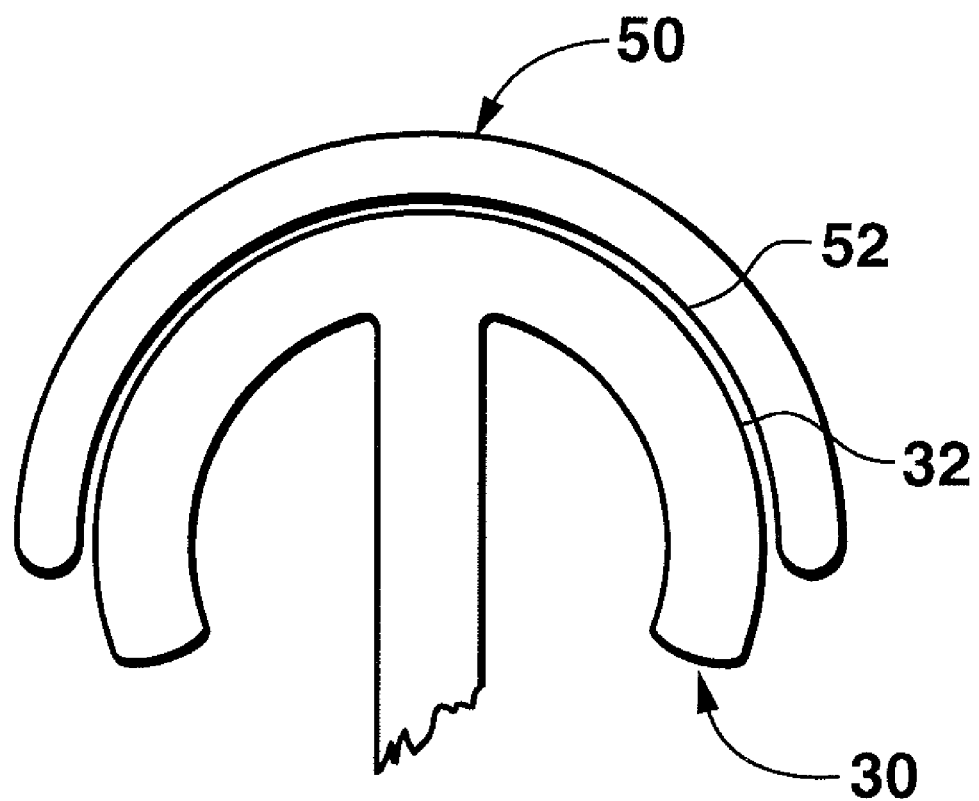
FIG. 1 is representative view of an orthopedic prosthesis incorporating the metal-on-metal differential hardness concepts of the present invention.

FIG. 1 provides a representative view of a hip prosthesis incorporating the differential hardness metal bearing concept of the invention. The prosthesis includes a first component 30 having a first bearing surface 32, and a second component 50 having a second bearing surface 52. The bearing surfaces 32, 52 are sized and configured to articulate relative to one another in the manner of a natural joint. For example, in FIG. 1, the first bearing surface 32 is convex while the second bearing surface 52 is concave, such that the first 32 and second 52 bearing surfaces articulate relative to one another in the manner of a hip or shoulder prosthesis. In a preferred embodiment, the concave bearing surface is a soft metal bearing surface and the convex bearing surface is a hard metal bearing surface. However, the concave bearing surface may be the hard metal bearing surface and the convex bearing surface may be the soft metal bearing surface.

The soft metal bearing surface preferably has a hardness of between about 25 Rc to about 35 Rc. The hard metal bearing surface preferably has a hardness of between about 40 to about 60 Rc.

Cobalt chrome alloys are the preferred metal for use in the invention. Cobalt chrome has good wear properties and can be accurately configured to provide desired sphericity, clearance and surface finish. The differential hardness concept of the invention can be applied to all medical grade CoCrMo alloys that have been approved by the FDA for medical devices. The soft metal bearing surface preferably has a carbon content of 0.2 to 0.25 percent-by-weight. The hard metal bearing surface preferably has a carbon content of 0.2 to 0.3 percent-by-weight, but low carbon alloys (less than 0.10 percent-by-weight) may be used. The differential hardness concept of the invention can be applied to CoCrMo alloys that have little or no carbon content.

The preferred diameters of the bearing surfaces will match those of existing prostheses. In the case of hip prostheses, the preferred diameter will generally fall between about 20 to 60 mm, with preferred ranges further varying depending on the type of hip prosthesis.

The first and second components of the prosthesis of the invention can be made entirely of the metal that provides the bearing surfaces. Alternatively, in one or both of the components, the material of the bearing surfaces may provide only a portion of the components. For example, the spherical head of the femoral component of a hip prosthesis may be formed of cobalt chrome, with the spherical head having a tapered hollow for receiving a tapered pin of the main body part of the femoral component. The acetabular component can be manufactured as a separate shell and insert, with the insert providing the bearing surface.

The differential hardness concept of the invention can be applied to a modular hip prosthesis of the type described in U.S. Pat. No. 4,957,510 (Cremescoli) and its European counterpart, EP0310566B1, both of which are incorporated herein by reference. Thus, the prosthesis could be provided with a spherical head configured to engage an end of a separate neck member.

An example of a modular neck embodiment is shown in FIGS. 4-15, which are also shown in U.S. Pat. No. 4,957,510. With reference to FIGS. 4-15, the hip prosthesis structure essentially comprises a stem 1 consisting of a flat bar having a given length. The surface of the stem 1 may be provided with a plurality of longitudinal slots 2. In the embodiment shown in FIG. 4, the stem 1 extends according to a suitably curved longitudinal axis and has a bottom end 3 of substantially oval shape. The stem 1 is provided, at the top thereof, with a portion 4 enlarged at the side of its concave perimetrical line on which there is formed a seat or recess 5 having a suitably slanted axis, an oval cross-section, and suitable taper. As shown in FIG. 5, the seat 5 preferably has a "race track" configuration in cross-section, with opposing flat sides and opposing curved portions. As shown in FIGS. 4-6, the enlarged portion 4 may have a grooved slanted face in which there are formed a plurality (three in the shown embodiment) of spaced grooves which have been specifically designed for receiving bone in-growth so as to provide, in cooperation with the slots 2, a very firm gripping of the stem 1 in the femur (not shown). As indicated in FIGS. 4 and 6, the seat 5 is configured to firmly house a stem end 6 of a coupling member or modular neck 7. The stem end 6 is also of oval cross-section. A femoral head end 8 of the modular neck 7 has a frustum of cone shape or Morse taper to firmly restrain a spherical head 9 (corresponding to bearing 30) adapted in turn for coupling with the acetabulum of the pelvis of the patient. The modular neck 7 may have any desired variable length, depending on the specific use requirements.

The modular neck 7 may have a differently slanted axis with respect to its stem end 6, with the axis of the stem end 6 coinciding with the axis of the seat 5. This slanting can be essentially obtained according to any of the planes pertaining to the plane set passing through the line defining the axis of the seat 5. FIGS. 8-12 show examples of possible configurations of modular necks 7 adapted to be applied on the prosthesis stem 1 and having different extension longitudinal axes. FIG. 8 shows a straight modular neck 7 in which the axis of the femoral head end 8 is coincident with the axis of the seat 5. FIG. 9 shows a varus modular neck 7 in which the axis of the femoral head is offset toward the midline from the axis of the seat 5. FIG. 10 shows a retroverted modular neck in which the axis of the femoral head 8 is offset posteriorly from the axis of the seat 5. FIG. 11 shows an anteverted modular neck in which the axis of the femoral head 8 is offset anteriorly from the axis of the seat 5. As is shown in FIG. 12, an embodiment of the present invention provides for the use of a modular neck/coupling member 7 including an insertion end 6 which is offset from its axial extension 8. Thus, a prosthesis will be formed including a coupling member 7 which virtually constitutes an extension of the middle curvature, indicated at 10, of the top portion of the stem 1. This configuration will afford the possibility of inserting a coupling member 7 even in prostheses 1 of minimum thickness, while assuring a perfect and reproducible positioning of the stem-coupling member assembly, without any risks of a possible disengaging of the two parts.

FIGS. 13-15 show another possible embodiment in which, at the enlarged end of the stem 1, there is provided a lug 20 which has a substantially tapering shape and an elliptical cross-section. From the lug 20 a cylindrical portion 21 may project, the cylindrical portion 21 being arranged on the axial extension of said lug 20. More specifically, the lug 20 can be engaged and firmly locked in a counter-shaped hollow 22, formed at the axial end portion of a coupling member 23 of the prosthesis. If desired the hollow 22 may be provided with a recess 24 for housing the mentioned cylindrical portion 21.

One object of the invention is to reduce manufacturing costs by providing differential hardness bearings surfaces in which each of the opposing articulating surfaces is manufactured from a cobalt chrome alloy that is currently approved for orthopedic implant applications, thus reducing manufacturing steps. However, it would be possible to provide the hardened component of differential bearing systems in alternative ways. The hardened component of a differential hardness bearing system may be provided as a surface layer using techniques such as vapor deposition of metal oxides or of ion bombardment to produce a mixed metal-ceramic matrix at the surfaces. Alternatively, the layer may be formed by heat treating such that a greater degree of hardness is conferred on the bearing surface than on underlying metal. The bearing layer may either be discrete or gradually transition to the base metal.

Testing

This invention, including the unexpected results described below, resulted from wear testing that was initiated by Wright Medical with the goal of finding the lowest wearing bearing coupling possible using materials currently approved for orthopedic implant applications. Before testing differential hardness MOM bearings, Wright Medical tested COM bearing combinations to determine wear rates. As expected, Wright observed reduced wear rates for COM hip prostheses in comparison to published MOM wear rates. Noting that COM hip prostheses typically have a hardness differential of about 4× between the ceramic and metal bearing surfaces, the inventor hypothesized that there may be a lower limit to the ability of differential hardness bearings to provide improved wear performance. The limit of differential hardness in relation to wear improvement has not been defined. Many wear models for hardness include only one value for hardness in the description equation, and therefore cannot take into account the effect of using bearings of different hardness.

In order to investigate the lower limit for hardness differentials, Wright Medical decided to test CoCr MOM hip prostheses having a relatively low hardness differential between the head and shell. At the beginning of testing, it was thought that CoCr MOM prostheses having a relatively low hardness differential might demonstrate slightly better wear properties than existing MOM bearing combinations. In fact, as discussed below, testing yielded the unexpected result that hip prostheses manufactured from CoCr alloys having a hardness differential produce wear results comparable to those obtained with COM prostheses.

To test wear in the lower limit of differential hardness, wear tests were conducted on the following combinations of femoral head and acetabular cup materials:

1. Cast and thermally treated CoCr-Head and Cup (ASTM F75 for both head and cup; Rc=25-30 for both head and cup; hardness differential=1.0×; n=7)
2. Cast CoCr head/Cast CoCr cup (ASTM F75 for both head and cup; Rc=25-30 for both head and cup; hardness differential=1.0×; n=3)
3. Wrought CoCr head/Cast-thermally treated CoCr cup (ASTM 1537 head/ASTM F75 cup; Rc=42 for head/25 for cup; hardness differential=1.68×; n=3)
4. Heat treated wrought CoCr head/Cast-thermally treated CoCr cup (ASTM F1537HT head/ASTM F75 cup; Rc=50-52 for head/25 for cup; hardness differential=2.08×; n=2)

Wear testing was conducted to typical WMT wear test protocols for hip wear testing using a SHORE WESTERN OBM wear test machine (90% Bovine serum lubricant; triple-peak Paul profile (2000 N max @ 1 Hz); specimens in the inverted position (head above/shells below)). Specimens were weighed at specific intervals to determine mass loss. All specimens were 54 mm in diameter. The material combination described in group 1 above is currently used for Wright Medical's CONSERVE® PLUS MOM hip prosthesis. The combination of Group 1 produces low wear in comparison to metal-on-polymer and competitive MOM prostheses. However, as mentioned above, some surgeons remain apprehensive about using MOM prostheses due to potential side effects from metal ion release from wear debris, and there is thus an interest in further reducing wear.

In groups 3 and 4, Wright's typical CONSERVE® PLUS acetabular cups (the same type of cups that were used in group 1) were tested against femoral heads made from wrought CoCr. The femoral heads of Group 3 were manufactured from BIODUR CCM+MICROMELT™ CoCrMo bar (available from Carpenter Technology of Reading, Pa.) in the as-received condition, which had a hardness of 42 Rc. The femoral heads of Group 4 were manufactured from BIODUR CCM+MICROMELT™ CoCrMo bar in a heat treated condition (24 hours at 1350 degrees Fahrenheit in air), which resulted in a hardness of about 50 to 52 Rc. The wrought as-received bar and the wrought heat-treated bar provided a differential hardness when compared to Wright Medical's typical acetabular cup (Rc=25). This difference in hardness was in the range of about 1.5 to 2×. As mentioned above, the hardness differential for ceramic-metal bearing combinations is typically on the order of 4× and can range from about 3× to 5× or even higher.

Figure 2:
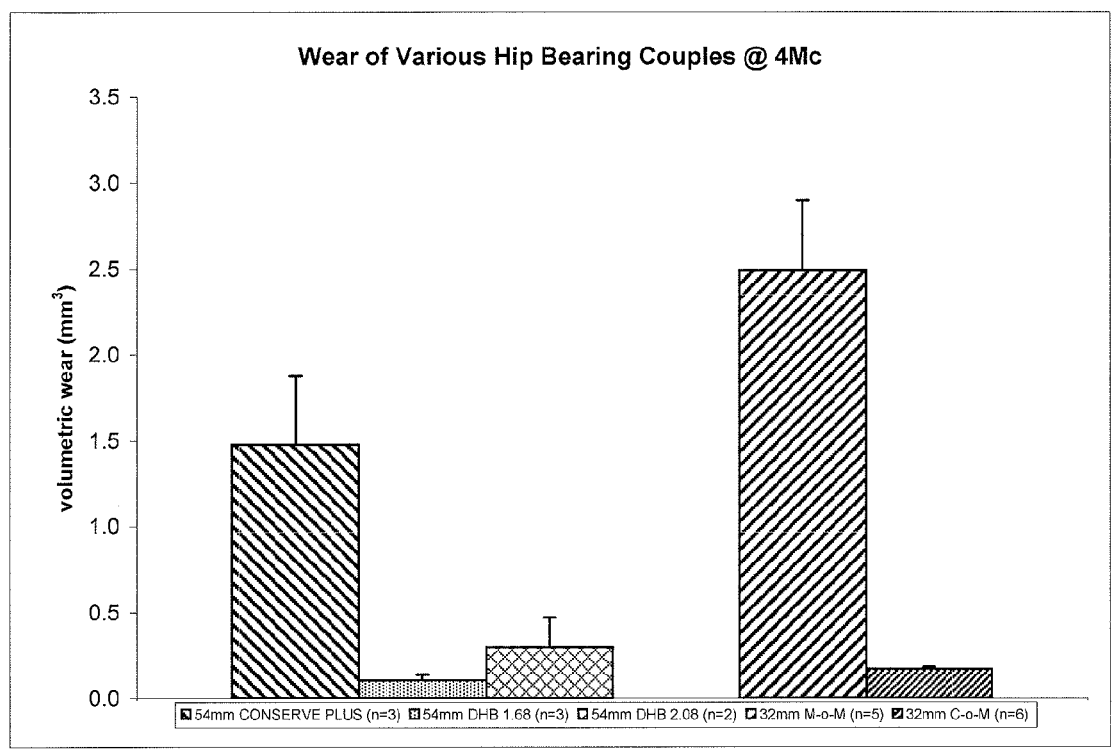
FIG. 2 is a graph demonstrating the wear of a differential hardness MOM hip prosthesis according to the invention in comparison with wear for conventional MOM and COM hip prostheses.
Figure 3:
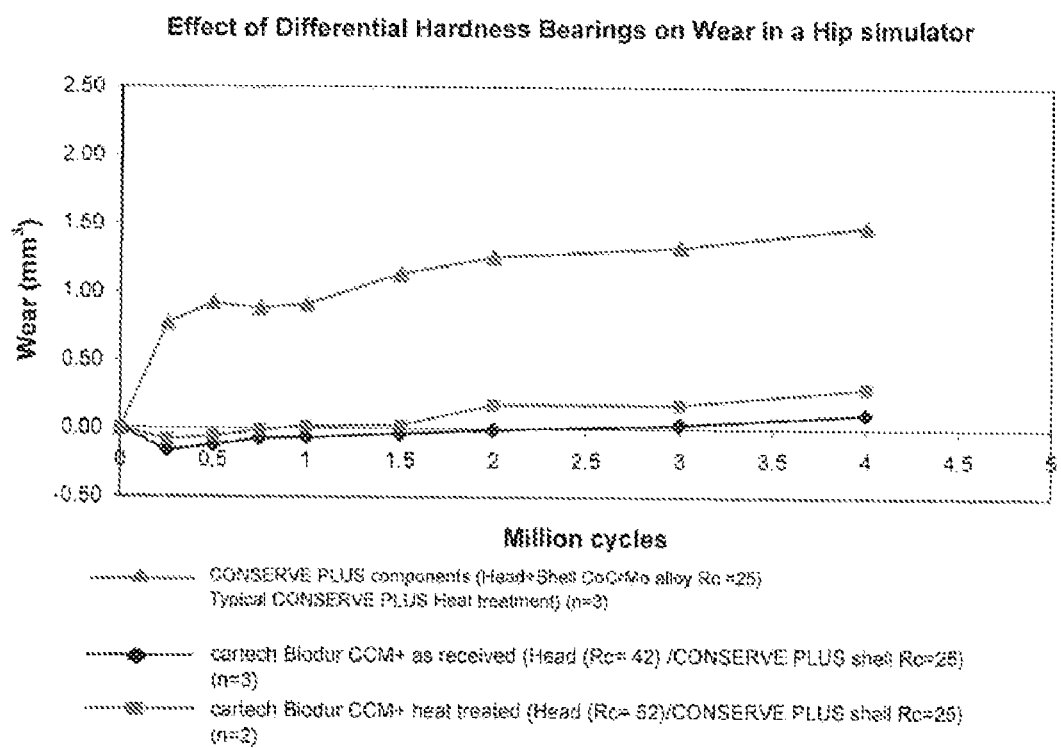
FIG. 3 is a graph demonstrating the wear rates of a differential hardness MOM hip prosthesis according to the invention in comparison with wear rates for a conventional MOM prosthesis of equal hardness.

Test results are shown in the graphs of FIGS. 2 and 3. The test results of FIGS. 2 and 3 demonstrate several unexpected properties of differential hardness MOM hip prostheses bearings: (1) significantly lower wear versus conventional MOM prostheses of the same type and size; (2) wear ratios that match those of COM prostheses when compared to conventional MOM prostheses of the same size and type; (3) overall wear matching or exceeding overall wear for COM prostheses; and (4) elimination of a bedding-in phase.

As shown in FIG. 2, the differential hardness metal bearings exhibited much lower wear than Wright's conventional CONSERVE® PLUS MOM femoral prosthesis. While a slight decrease in wear was expected for the differential hardness MOM bearings versus the conventional CONSERVE® PLUS MOM prosthesis, the magnitude of the reduction was surprising. The Group 3 MOM prostheses having a hardness differential of 1.68× showed only about 0.107 mm$^3$ of wear during the entire test. The Group 2 MOM prostheses having a hardness differential of 2.08 showed only about 0.298 mm$^3$ of wear during the entire test. In contrast, CONSERVE® PLUS MOM prosthesis having a conventional hardness differential of 1.0× demonstrated total wear of about 1.478 mm$^3$ during the test. Thus, the Group 3 CoCr MOM bearings demonstrated approximately 14× lower wear than the CONSERVE® PLUS MOM bearings of identical size (54 mm). The Group 4 CoCr MOM bearings demonstrated approximately 5.0× lower wear than the conventional CONSERVE® PLUS MOM bearings of identical size (54 mm). The test results were also surprising in comparison with published data for MOM hip prostheses. For example, Firkins (discussed above), using different test methods, had shown MOM wear rates of about 8 mm$^3$ after four million cycles.

Unexpectedly, when the differential hardness CoCr MOM bearings and COM bearings were compared to conventional MOM bearings of the same size and type, the differential hardness CoCr MOM and the COM bearings exhibited similar reductions in wear. FIG. 3 shows that COM bearings tested by Wright Medical exhibited about a 14.5× reduction in wear as compared to a conventional MOM system of identical size (32 mm). As mentioned above, the Group 3 CoCr MOM bearings having a hardness differential of 1.68× demonstrated approximately 14.0× lower wear than typical CONSERVE® PLUS MOM bearings of identical size (54 mm).

In terms of overall wear, the wear of the Group 3 differential hardness MOM bearings was on average lower than that of the COM bearings (0.107 mm$^3$ for differential MOM versus 0.172 mm for COM). Although the Group 4 differential hardness MOM bearings did not match wear results for COM bearings, the overall wear of the Group 4 bearings was on the same order of magnitude as COM bearings (0.298 mm$^3$ for 2.08× differential MOM versus 0.172 mm$^3$ for COM). This represented a significant reduction over the conventional CONSERVE® PLUS MOM bearings, which showed almost a ten fold increase in wear versus COM bearings (1.478 mm$^3$ versus 0.172 mm$^3$). As mentioned above, the brittleness and lower toughness of ceramic materials make it difficult to manufacture large diameter ceramic heads (e.g. 54 mm) of the type used in hip resurfacing procedures. The invention solves this problem by allowing for the manufacture of hip prostheses that match the wear rates of COM bearings while essentially eliminating the risk of fracture associated with ceramics, a result that could have particular significance for large size hip prostheses.

As shown in FIG. 3, the differential hardness metal bearings also exhibited no bedding-in phase. This result was also unexpected because, as mentioned above, it was previously accepted that MOM prostheses have a bedding-in phase (see e.g. WO 0117464A1 reported a bedding in rate of 3.12±0.45 mm$^3$/10$^6$ cycles; see also Firkins). As shown in FIG. 3, Wright's CONSERVE® PLUS MOM prosthesis exhibited a bedding-in wear phase of about 3.1 mm$^3$ While a slight reduction in bedding-in rate was expected for differential hardness MOM bearings, elimination of the bedding-in phase was a surprising result. Since the bedding-in phase produces in a large amount of metal particulates, elimination of the bedding-in phase is significant to patients who receive prostheses implants.

There are several reasons why the wear data presented in FIGS. 2 and 3 is unexpected. The difference in hardness for the MOM bearing combination was half that of the COM system, which suggested that wear rates would be significantly higher for differential hardness MOM bearings than for COM bearings. The MOM hardness differential was achieved over a low hardness range (about 25-50 Rc for the MOM bearings), whereas COM prostheses achieve differential hardness over a large hardness range. CoCr alloy is less abrasion resistant than ceramic. All of the foregoing factors suggested that wear rates should have been significantly higher for differential hardness MOM bearings than for COM bearings, a result that would have been consistent with published results on MOM wear rates. As mentioned above, while a slight decrease in wear was expected for the differential hardness bearings, the magnitude of the reduction was surprising.

Additionally, the prior art taught away from any suggestion that MOM prostheses, much less prosthesis bearings manufactured from alloys currently approved for use in prostheses, could achieve wear levels comparable to COM prostheses. For example, Firkins reported wear rates for MOM prostheses that showed a 100 fold higher degree of wear than for COM prostheses. Id. at 1296 (discussed above). There is no suggestion in Firkins or elsewhere that a MOM prosthesis could achieve wear levels comparable to COM prostheses. Yet, surprisingly, the results reported in FIG. 2 are similar to Firkins' reported wear rates for COM hip prostheses. Id. at 1294. The differential hardness bearing concept of the present invention thus produces unexpected results.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A hip prosthesis comprising:
   a spherical bearing member, said spherical bearing member having a neck recess therein,
   a femoral stem, said femoral stem having a recess adjacent a proximal end thereof,
   a modular neck member, a proximal end of said modular neck member configured to fixedly engage said neck recess of said spherical bearing member, a distal end of said modular neck member configured to fixedly engage said recess of said stem,
   an acetabular implant having a concave bearing surface configured for articulation with said spherical bearing member,
   wherein one of said spherical bearing member and said concave bearing surface comprises a soft metal bearing surface of cobalt chrome alloy, said soft metal bearing surface having a hardness of at least about 20 Rc, and
   wherein said other one of said spherical bearing member and said concave bearing surface comprises a hard metal bearing surface of cobalt chrome alloy, said hard metal bearing surface having a hardness greater than said soft metal bearing surface by at least about 15 Rc, such that there is a hardness differential between said spherical member and said concave bearing surface to thereby reduce wear of said hip prosthesis.

2. The prosthesis of claim 1, wherein the differential hardness of said hard metal bearing surface to said soft metal bearing surface is at least about 1.5.

3. The prosthesis of claim 1, wherein the differential hardness of said hard metal bearing surface to said soft metal bearing surface is between about 1.5 and about 3.

4. The prosthesis of claim 1, wherein said hard metal bearing surface is not more than about 40 Rc harder than said soft metal bearing surface.

5. The prosthesis of claim 1, wherein said hard metal bearing surface has a hardness of between about 40 Rc and about 60 Rc.

6. The prosthesis of claim 1, wherein said spherical bearing member comprises said hard metal bearing surface and said concave bearing member comprises said soft metal bearing surface.

7. The prosthesis of claim 1, wherein said cobalt chrome alloy of said soft metal bearing surface conforms to ASTM F75 and said cobalt chrome alloy of said hard metal bearing surface conforms to ASTM 1537.

8. The prosthesis of claim 1, wherein said hard metal bearing surface is heat treated to increase hardness of said hard metal bearing surface.

9. The prosthesis of claim 1, wherein said spherical bearing member has a diameter of between about 40 mm to about 60 mm.

10. The prosthesis of claim 1, wherein said spherical bearing member has a diameter of about 54 mm.

11. The prosthesis of claim 4, wherein said hard metal bearing surface has a hardness of between about 40 Rc and about 60 Rc.

12. The prosthesis of claim 11, wherein said spherical bearing member comprises said hard metal bearing surface and said concave bearing member comprises said soft metal bearing surface.

13. The prosthesis of claim 12, wherein said cobalt chrome alloy of said soft metal bearing surface conforms to ASTM F75 and said cobalt chrome alloy of said hard metal bearing surface conforms to ASTM 1537.

14. The prosthesis of claim 1, wherein said soft metal bearing surface has a hardness of between about 25 Rc to about 35 Rc.

15. The prosthesis of claim 1, wherein said recess of said femoral stem is tapered.

16. The prosthesis of claim 15, wherein said recess of said femoral stem has an oval cross-section.

17. The prosthesis of claim 15, wherein said recess of said femoral stem has a race track configuration in cross-section, said race track configuration having opposing flat sides and opposing curved portions.

18. The prosthesis of claim 15, wherein an axis of said distal end of said modular neck is coincident with an axis of said recess of said femoral stem.

19. The prosthesis of claim 18, wherein an axis of said proximal end of said modular neck is axially aligned with an axis of said distal end of said modular neck.

20. The prosthesis of claim 18, wherein an axis of said proximal end of said modular neck is axially offset from an axis of said distal end of said modular neck.

* * * * *